(12) United States Patent
Petty et al.

(10) Patent No.: US 6,759,601 B1
(45) Date of Patent: Jul. 6, 2004

(54) CHECK WEIGHING APPARATUS AND METHOD

(75) Inventors: Michael Petty, Cambridge (GB); David Fathers, Cambridge (GB); Colin Nicholls, Guildford (GB); David Taylor, Guildford (GB); Valerie Scott, Cambridge (GB)

(73) Assignee: Scientific Generics Limited, Cambridgeshire (GB)

( * ) Notice: Subject to any disclaimer, the term of this patent is extended or adjusted under 35 U.S.C. 154(b) by 0 days.

(21) Appl. No.: 09/719,931

(22) PCT Filed: Jun. 24, 1999

(86) PCT No.: PCT/GB99/01992

§ 371 (c)(1),
(2), (4) Date: Jun. 4, 2001

(87) PCT Pub. No.: WO99/67606

PCT Pub. Date: Dec. 29, 1999

(30) Foreign Application Priority Data

Jun. 24, 1998 (GB) .............................................. 9813673

(51) Int. Cl.[7] .............................................. G01G 9/00
(52) U.S. Cl. ...................... 177/1; 177/210 R; 324/300; 73/433; 73/865
(58) Field of Search ...................... 177/1, 245, 210 R; 324/308, 300, 307; 73/865, 433, 580

(56) References Cited

U.S. PATENT DOCUMENTS

| | | | |
|---|---|---|---|
| 3,796,873 A | | 3/1974 | Ledgett ........................ 378/54 |
| 3,966,973 A | * | 6/1976 | Henry et al. .................. 324/307 |
| 4,556,847 A | * | 12/1985 | Aspiotis et al. ............. 324/307 |
| 4,720,808 A | * | 1/1988 | Repsch ........................... 177/1 |
| 5,184,733 A | * | 2/1993 | Arnarson et al. .............. 177/1 |
| 5,247,934 A | | 9/1993 | Wehrli et al. ................ 600/410 |
| 5,270,650 A | | 12/1993 | Schenz et al. .............. 324/308 |
| 5,291,422 A | | 3/1994 | Esztergar ...................... 702/30 |
| 5,550,537 A | * | 8/1996 | Perdue .................... 177/210 R |
| 5,585,603 A | * | 12/1996 | Vogeley, Jr. .................... 177/1 |

FOREIGN PATENT DOCUMENTS

| | | |
|---|---|---|
| DE | 18 03 372 A | 5/1970 |
| GB | 2 149 509 | 6/1985 |

OTHER PUBLICATIONS

*High Magnetic Fields: Applications, Generation, Materials*, Schneider–Muntau, Ed., World Scientific, London, pp. 9–19 Oct. 1999.*

"Hydrogen Transient Nuclear Magnetic Resonance for Industrial Moisture Sensing", C.I. Nicholls et al., pp. 849–873; Dept. Electronics and Physics, Southwest Research Institute, San Antonio, Texas. © 1991.

* cited by examiner

*Primary Examiner*—Randy Gibson
(74) *Attorney, Agent, or Firm*—Cohen, Pontani, Lieberman & Pavane

(57) ABSTRACT

A check weighing system is provided which can check weigh samples (1) on a production line. The check weighing system comprises a magnet (13) for creating a static magnetic field over an interrogation zone for creating a net magnetisation within a sample (1) located within the interrogation zone and an RF coil for applying an alternating magnetic field over the interrogation zone for causing excitation of the sample (1) within the interrogation zone according to the principles of NMR. The check weighing system also comprises a sensor for sensing the energy emitted as the sample relaxes back to an equilibrium state after excitation as the samples pass through the interrogation zone on a conveyor belt (9) forming part of the production line. The sensed signal from the sample (1) is then compared with calibration data which is obtained for at least one similar sample of known mass, which calibration data relates the mass of the similar sample to the corresponding signal output by the sensor, to provide the indication of the mass of the sample.

38 Claims, 7 Drawing Sheets

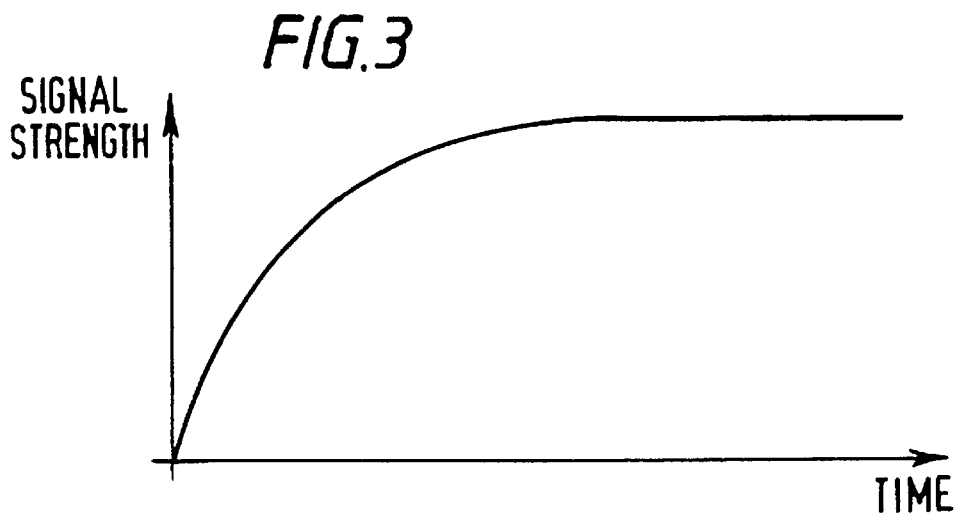
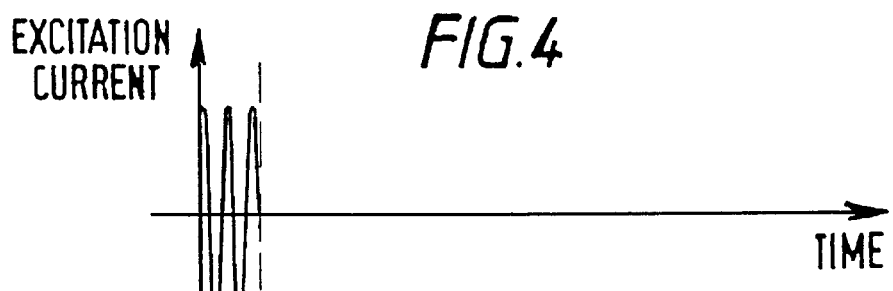
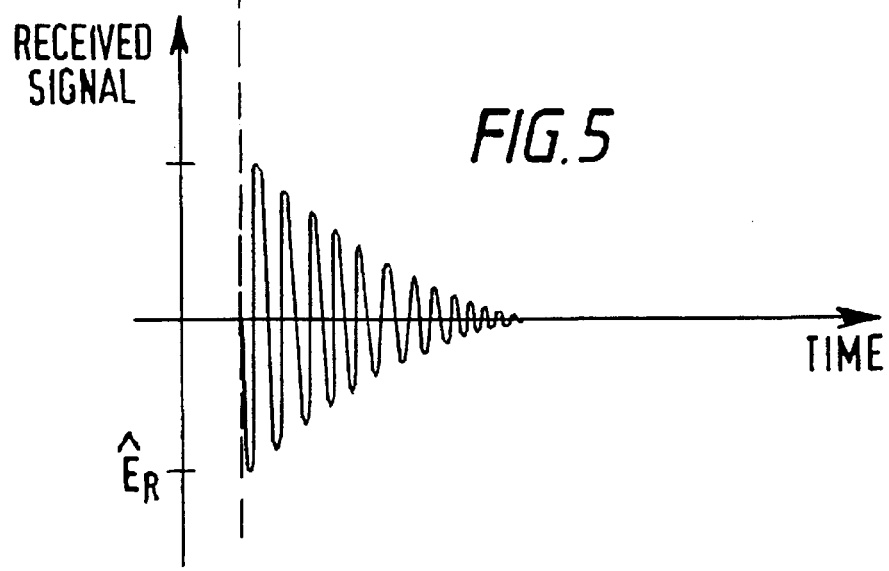

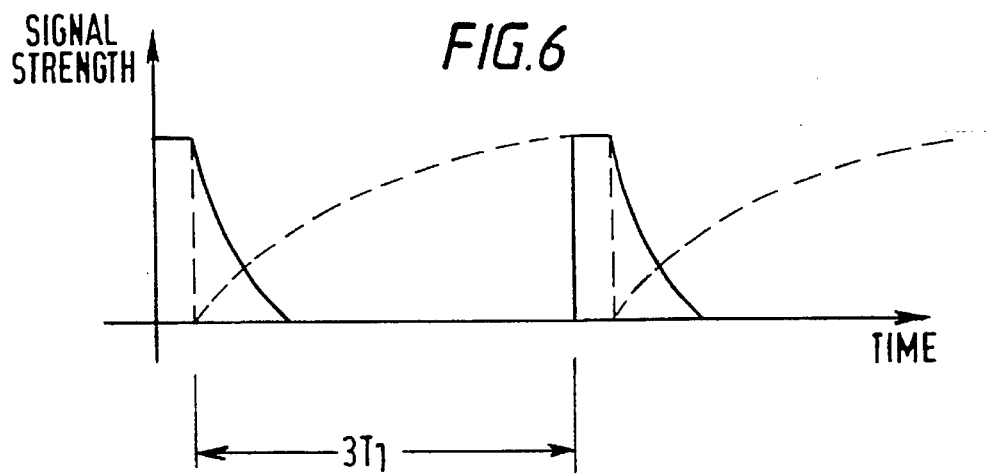
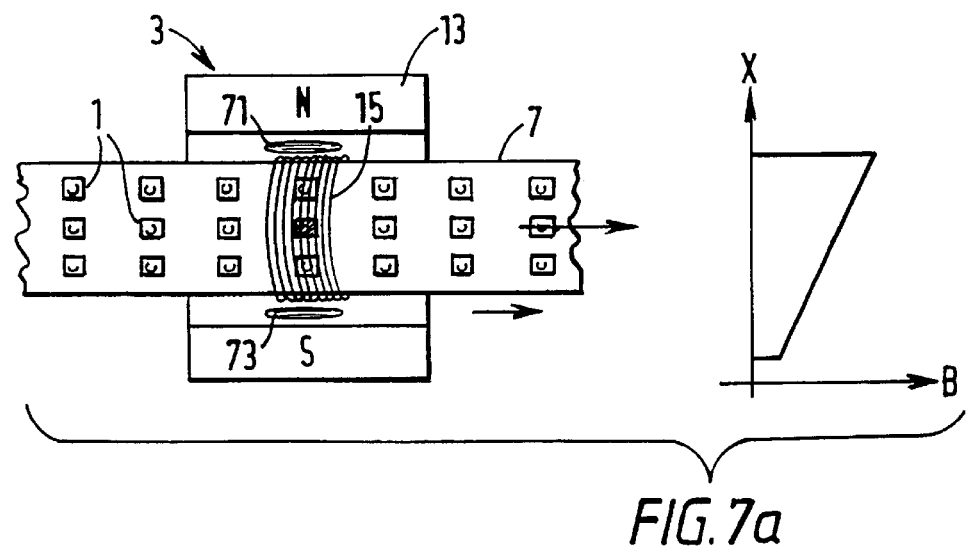

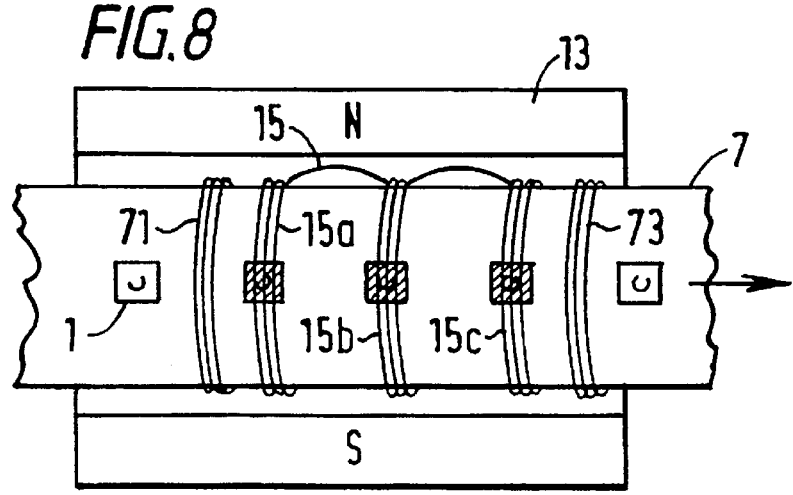
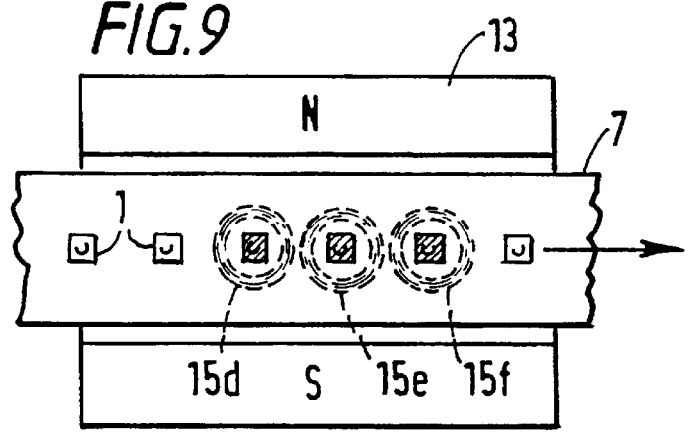
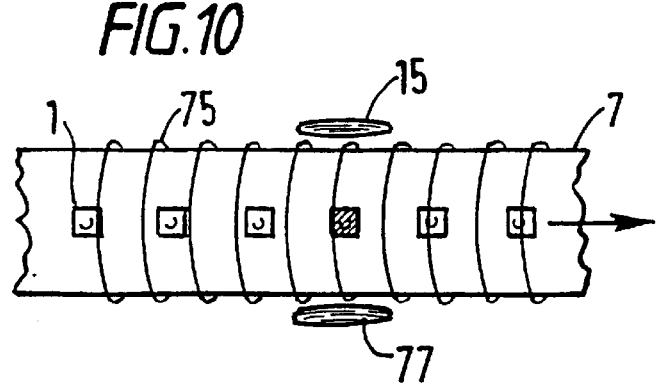

CHECK WEIGHING APPARATUS AND METHOD

This is a U.S. National Phase Application under 35 USC 371 of International Application PCT/GB99/01992, filed on Jun. 24, 1999.

The present invention relates to an apparatus and method for check weighing material contained in a container which is passing along a production line. The invention particularly relates to the use of magnetic resonance techniques for such check weighing.

In today's industrial environment there is a continuous need to improve efficiency, quality and yield. As a result, automated control and quality assurance (QA) systems for manufacturing lines are becoming increasingly important. One type of monitoring device commonly used on product filling lines is a check weighing device, which is used to ensure that the required amount of product is put in each container.

As one example, check weighing is used by the pharmaceuticals industry for the monitoring and regulation of the amount of a drug in a sealed glass vial during filling. The drug weight can be as small as a fraction of a gram, and is required to be weighed with an accuracy of a few per cent or better, in a vial weighing tens of grams at a rate of several weighings per second. At present, to obtain the required accuracy, it is necessary to remove the vials from the production line and to weigh them on precision balances. This must be done both before and after filling in order to take into account the weight of the container. Inevitably this is a time consuming process and 100% inspection cannot be achieved while maintaining throughput. As a result only a fraction of the product is ever tested. Therefore, if something does go wrong and the vials are not being filled with the correct amount of the drug, then a large batch of product can be wasted before the problem is even noticed. Furthermore, since the vial must be weighed both before and after filling, the weighing must be performed in the aseptic environment between filling and sealing.

The present invention aims to provide an alternative technique for check weighing products on a production line.

This and other objects are attained in accordance with one aspect of the invention directed to an apparatus for determining an on-line measure of the mass of each of a plurality of discrete samples in a production line. The apparatus includes a transporter operable to transport the plurality of discrete samples along a transport path through an interrogation zone. A static magnetic field generator is operable to generate a static magnetic field in a first direction through the interrogation zone for creating a net magnetisation within a current sample located within the interrogation zone. An alternating magnetic field generator is operable to apply a pulse of alternating magnetic field in a second different direction through the interrogation zone for temporarily changing the net magnetisation of the current sample located within the interrogation zone. A position sensor is operable to sense the position of each discrete sample on the transporter as it approaches the interrogation zone and operable to output a corresponding position signal. A controller is operable to control the timing of the application of the pulse of alternating magnetic field by the alternating magnetic field generator in dependence upon the position signal output by the position sensor so that the pulse of alternating magnetic field is applied when the current sample is in the interrogation zone. A sensor is operable to sense energy emitted by the current sample as the net magnetisation of the current sample returns to its original state and operable to output a sensor signal in dependence thereon. Processing circuitry is operable to process the sensor signal to determine a measure of the amplitude of the energy emitted by the current sample. A memory is operable to store predetermined calibration data defining a relationship between the amplitude measure and mass, which calibration data is obtained from an amplitude measure determined by the processing circuitry for one or more similar samples of known mass. A measuring device is operable to determine the measure of the mass of the current sample using the calibration data and the amplitude measure output by the processing circuitry for the current sample. The static magnetic field generator is operable to generate a static magnetic field which is substantially homogeneous over a length of the transport path so that each sample is exposed to the static magnetic field for a predetermined period of time before it reaches the interrogation zone.

Another aspect of the invention is directed to a method of determining an on-line measure of the mass of each of a plurality of discrete samples in a production line. The method includes transporting the plurality of discrete samples along a transport path through an interrogation zone, generating a static magnetic field in a first direction through the interrogation zone to create a net magnetisation within a current sample located within the interrogation zone, applying a pulse of alternating magnetic field in a second different direction through the interrogation zone to temporarily change the net magnetisation of the current sample located within the interrogation zone, and sensing the position of each discrete sample along the transport path as it approaches the interrogation zone and outputting a corresponding position signal. The method further includes controlling the timing of the application of the pulse of alternating magnetic field in dependence upon the position signal output in the position sensing step, so that the pulse of alternating magnetic field is applied when the current sample is in the interrogation zone, sensing energy emitted by the current sample as the net magnetisation of the current sample returns to its original state and outputting a sensor signal in dependence thereon, processing the sensor signal to determine a measure of the amplitude of the energy emitted by the current sample, storing predetermined calibration data defining a relationship between the amplitude measure and mass, which calibration data is obtained from an amplitude measure determined in the processing step for one or more similar samples of known mass, and determining the measure of the mass of the current sample using the calibration data and the amplitude measure output by the processing step for the current sample. The generating step generates a static magnetic field which is substantially homogeneous over a length of the transport path so that each sample is exposed to the static magnetic field for a predetermined period of time before it reaches the interrogation zone.

Yet another aspect of the invention is directed to a method of producing sealed containers containing a predetermined amount of a sample. The method includes filling the container with the predetermined amount of sample, sealing the sample within the container, transporting each of the filled containers along a transport path to a weighing station, weighing the sample within each of the containers, and rejecting any containers which do not contain the predetermined amount of sample within a predetermined tolerance. The weighing is accomplished by generating a static magnetic field in a first direction through an interrogation zone to create a net magnetisation within a sample located within the interrogation zone, applying a pulse of alternating magnetic field in a second different direction through the interrogation zone to temporarily change the net magnetisation of the current sample located within the interrogation zone, sensing the position of each discrete sample along the transport path as it approaches the interrogation zone and outputting a corresponding position signal, controlling the timing of the application of the pulse of alternating magnetic field in dependence upon the position signal output in the position sensing step, so that the pulse of alternating magnetic field is applied when the current sample is in the interrogation zone, sensing energy emitted by the current sample as the net magnetisation of the current sample returns to its original state and outputting a sensor signal in dependence thereon, processing the sensor signal to determine a measure of the amplitude of the energy emitted by the current sample, storing predetermined calibration data defining a relationship between the amplitude measure and mass, which calibration data is obtained from an amplitude measure determined in the processing step for one or more similar samples of known mass, and determining a measure of the mass of the current sample using the calibration data and the amplitude measure output by the processing step for the current sample. The generating step generates a static magnetic field which is substantially homogeneous over a length of the transport path so that each sample is exposed to the static magnetic field for a predetermined period of time before it reaches the interrogation zone.

A further aspect of the invention is directed to an apparatus for determining an indication of the mass of a sample. The apparatus includes a signal generator operable to generate a non-uniform electric field within an interrogation zone for interacting with a sample located within the interrogation zone, a sensor operable to sense nuclear quadrupole resonance signals generated by the interaction of the sample with the non-uniform electric field and for outputting a signal in dependence thereon, a memory operable to store predetermined calibration data for at least one similar sample of known mass, which calibration data relates the mass of the at least one similar sample to the corresponding nuclear quadrupole resonance signal output by the sensor; and a comparator operable to compare the nuclear quadrupole resonance signal output by the sensor with the calibration data to provide the indication of the mass of the sample.

Exemplary embodiments of the invention will now be described with reference to the accompanying drawings in which:

FIG. 3 is a plot which illustrates how the net magnetisation of a sample varies with the time it is subjected to a static magnetic field which forms part of the check weighing station shown in FIG. 1;

FIG. 4 is a plot of a pulse of excitation current which is applied to an excitation coil which forms part of the check weighing station shown in FIG. 1;

FIG. 5 is a plot which shows the way in which the signal generated by a sample decays after the pulse of excitation current shown in FIG. 4 ends;

FIG. 6 is a plot illustrating the time required between sample measurements of the same sample;

Figure 7B:
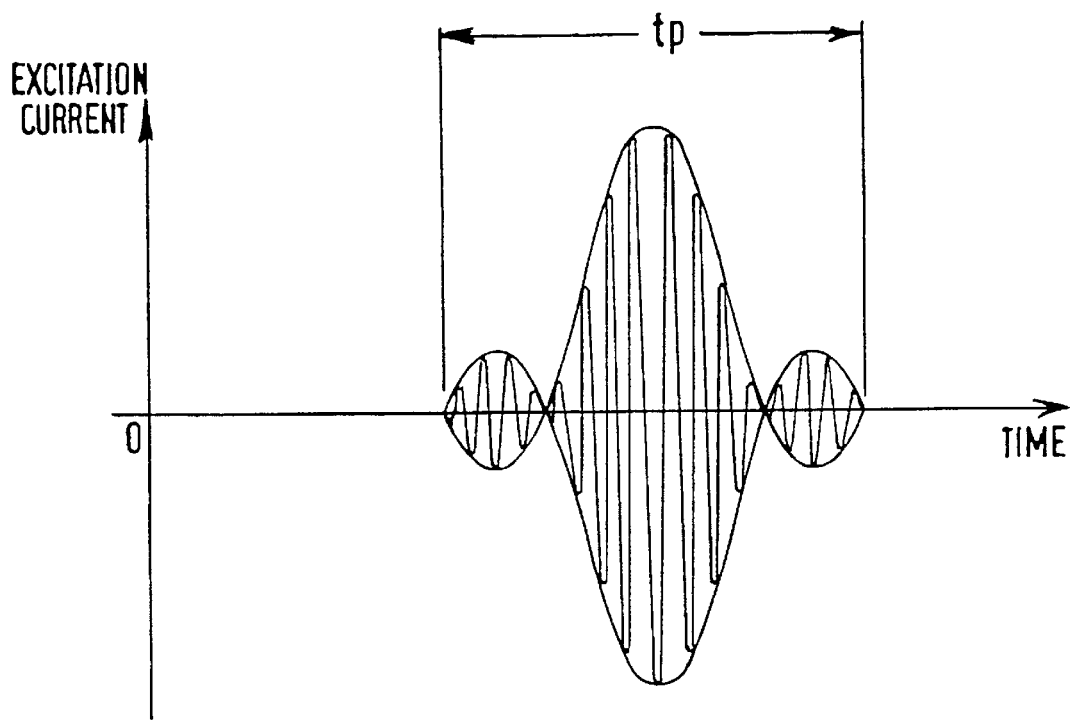
Figure 7C:
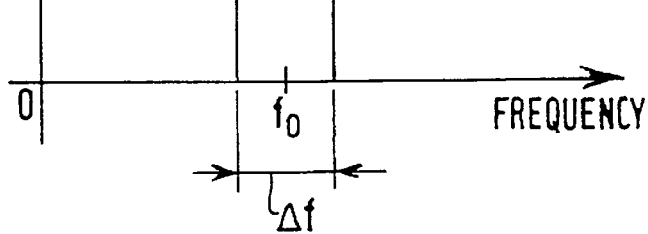
Figure 11:
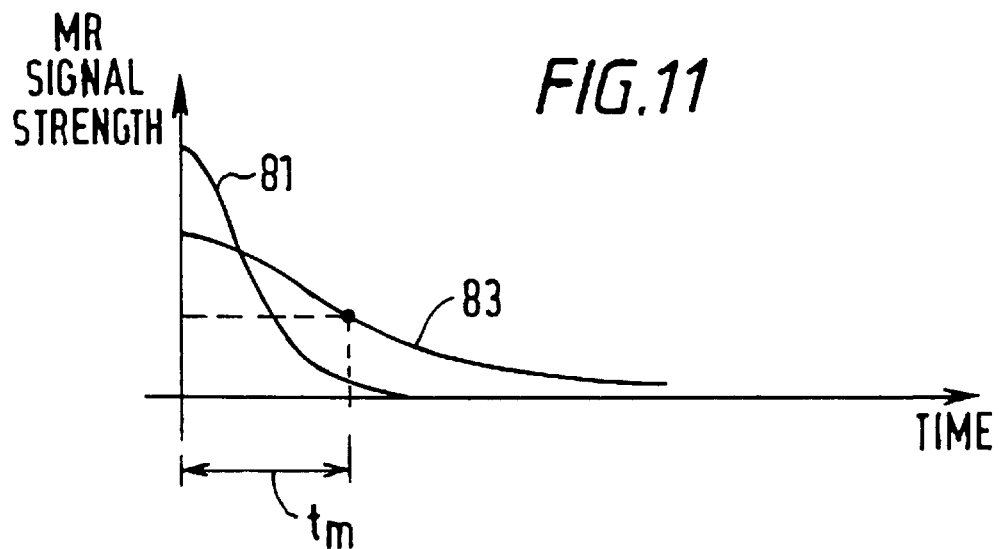
Figure 12:
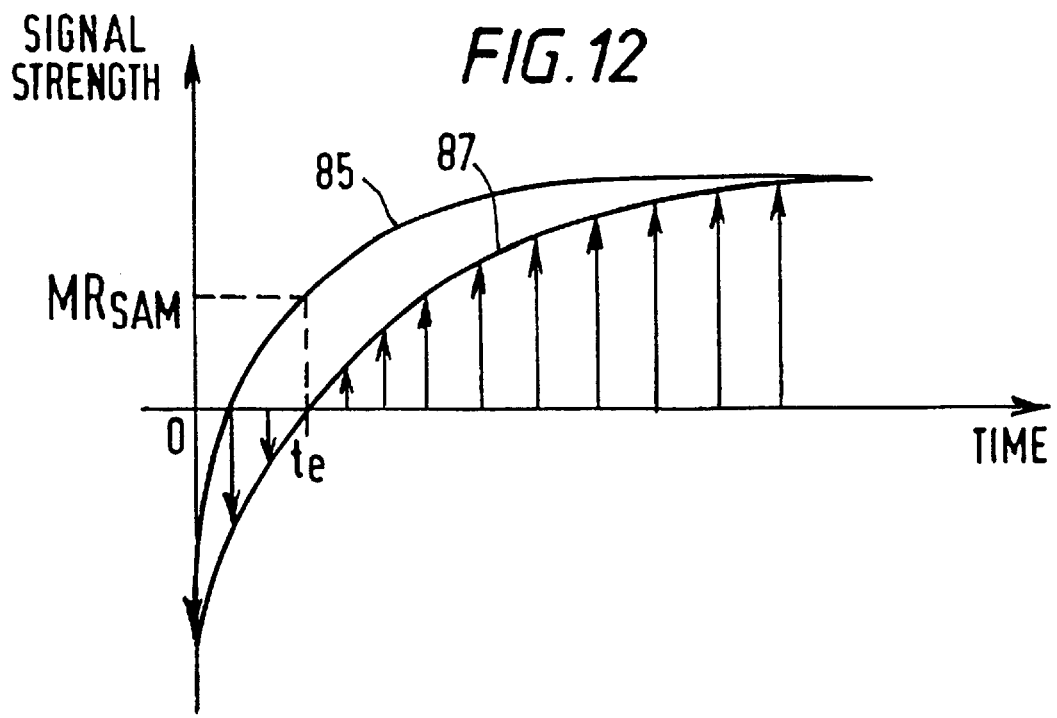

FIG. 7a diagrammatically illustrates the form of a check weighing station according to an alternative embodiment in which a magnetic field gradient is applied over an interrogation zone;

FIG. 7b illustrates the form of a narrow bandwidth pulse which is applied to the RF coil shown in FIG. 7a for interrogating a selected region of the interrogation zone;

FIG. 7c illustrates the narrow bandwidth of the pulse shown in FIG. 7b;

FIG. 8 diagrammatically illustrates the form of a check weighing station according to another embodiment of the present invention;

FIG. 9 illustrates the form of yet a further check weighing station embodying the present invention;

FIG. 10 illustrates the form of another check weighing station embodying the present invention;

FIG. 11 is a plot of the signal strengths generated by a sample under test and a seal used to close the vial in which the sample is contained; and FIG. 12 is a plot of the signal strength generated by the sample under test and the seal of the vial in which the sample is contained after an inversion excitation pulse is applied to the vial.

Figure 1:
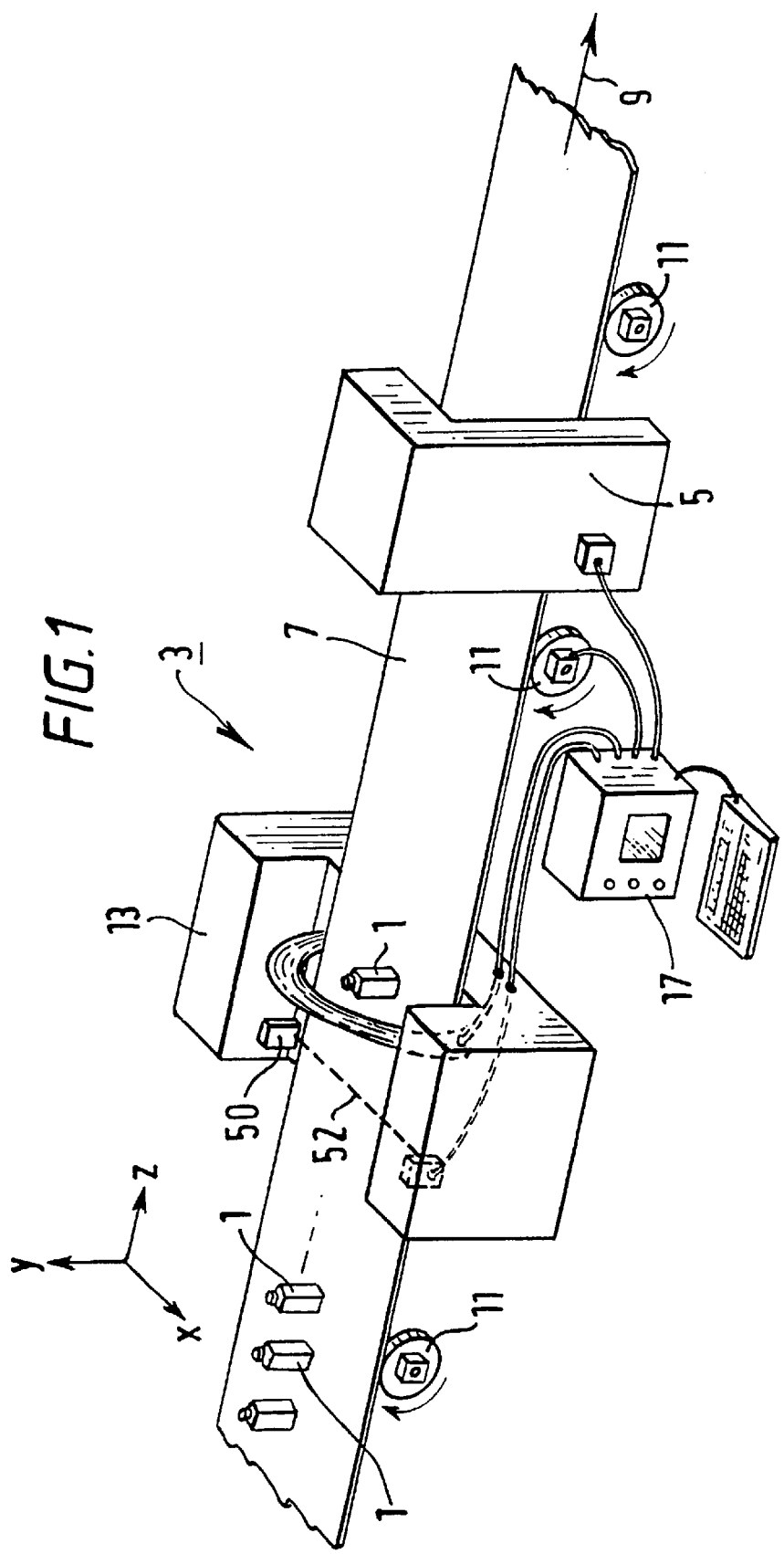
FIG. 1 is an overview of a production line with a magnetic resonance check weighing station for checking that each filled vial which passes through the weighing station has the required amount of product.

FIG. 1 shows part of a production line which fills glass vials 1 with a drug sample. In particular, FIG. 1 shows the weighing station 3 which is provided "in-line" for weighing each of the filled vials which pass therethrough. FIG. 1 also shows a reject station 5 which removes those vials from the line which do not have a sufficient amount of the drug to meet regulatory requirements. As shown, the vials 1 are transported to the weighing station 3 from a filling and sealing station (not shown) by a conveyor belt 7 which, as represented by the arrow 9, moves in the z direction through the action of the rotating conveyor wheels 11.

As mentioned above, the present invention uses magnetic resonance (MR) techniques to determine the mass of the drug sample within each of the glass vials 1. As those skilled in the art of MR will appreciate, glass vials are used as the container in this embodiment, because they do not give off an MR signal which might interfere with the measurement process. In this embodiment, the weighing station 3 comprises a permanent magnet 13, an RF coil 15 and a computer control system 17. The magnet 13 is used to create a homogeneous DC or static magnetic field in the x direction across the conveyor belt 7. The sample in the glass vial contains nuclei which each possess a magnetic moment, e.g. $^1H$ nuclei (protons). This magnetic moment is a result of the spin of the nuclei. The magnetic moment acts like a small bar magnet and its strength is dependent on the type of nuclei. Before the sample is placed in the static magnetic field, the individual nuclear magnetic moments are randomly orientated. When they enter the static magnetic field, they tend to align with the static field, along the X-direction in this case. The magnetic moments can align themselves either parallel or anti-parallel to the static field. Alignment parallel to the static field is the lower energy state and thus more of the magnetic moments adopt this orientation. This results in the sample having a resultant net macroscopic magnetisation parallel to the static field.

As mentioned above, the nuclei possess spin and, as a result of this, they rotate or precess around the static magnetic field. The frequency of this precession is known as the Larmor frequency and is dependent on the strength of the static magnetic field. In particular, it can be defined as follows:

$$\text{frequency} = \gamma \cdot B \qquad (1)$$

where γ is the gyromagnetic ratio of the sample and B is the magnetic field strength of the static magnetic field generated by the magnet 13. The gyromagnetic ratio (γ) is related to the strength of the magnetic moment for the nucleus in question. For example, the gyrometric ratio for protons is 42.57 MHz/Tesla.

In the majority of magnetic resonance systems, the static magnetic field strength is such that the Larmor frequency of the sample is in the radio frequency range of the electromagnetic spectrum. As those skilled in the art of magnetic resonance will appreciate, applying an AC magnetic field to the sample at the sample's Larmor frequency and orientated orthogonal to the static magnetic field, will cause the sample's net magnetisation to rotate about the AC magnetic field's axis, away from the direction of the static field. In this embodiment, this magnetic field is generated by applying a corresponding AC current to the RF coil 15. The angle of rotation of the net magnetisation can be varied by varying the amount of energy delivered to the RF coil 15. In this embodiment, an excitation field which causes a 90° rotation is used to excite the sample. After the 90° pulse has been applied to the sample, the sample is left in a high-energy, non-equilibrium state, from which it will relax back to its equilibrium state. As it relaxes, electromagnetic energy at the Larmor frequency is emitted, the magnetic component of which induces current in the RF coil 15, the peak amplitude of which varies with, among other things, the number of magnetic moments in the sample and hence the number of molecules in the sample. The received signal is then passed to the computer control system 17 which compares the peak amplitude of the signal received from the unknown sample with the peak amplitude of a signal received from a sample with a known mass (or weight), to determine the mass (or weight) of the sample being tested.

Figure 2:
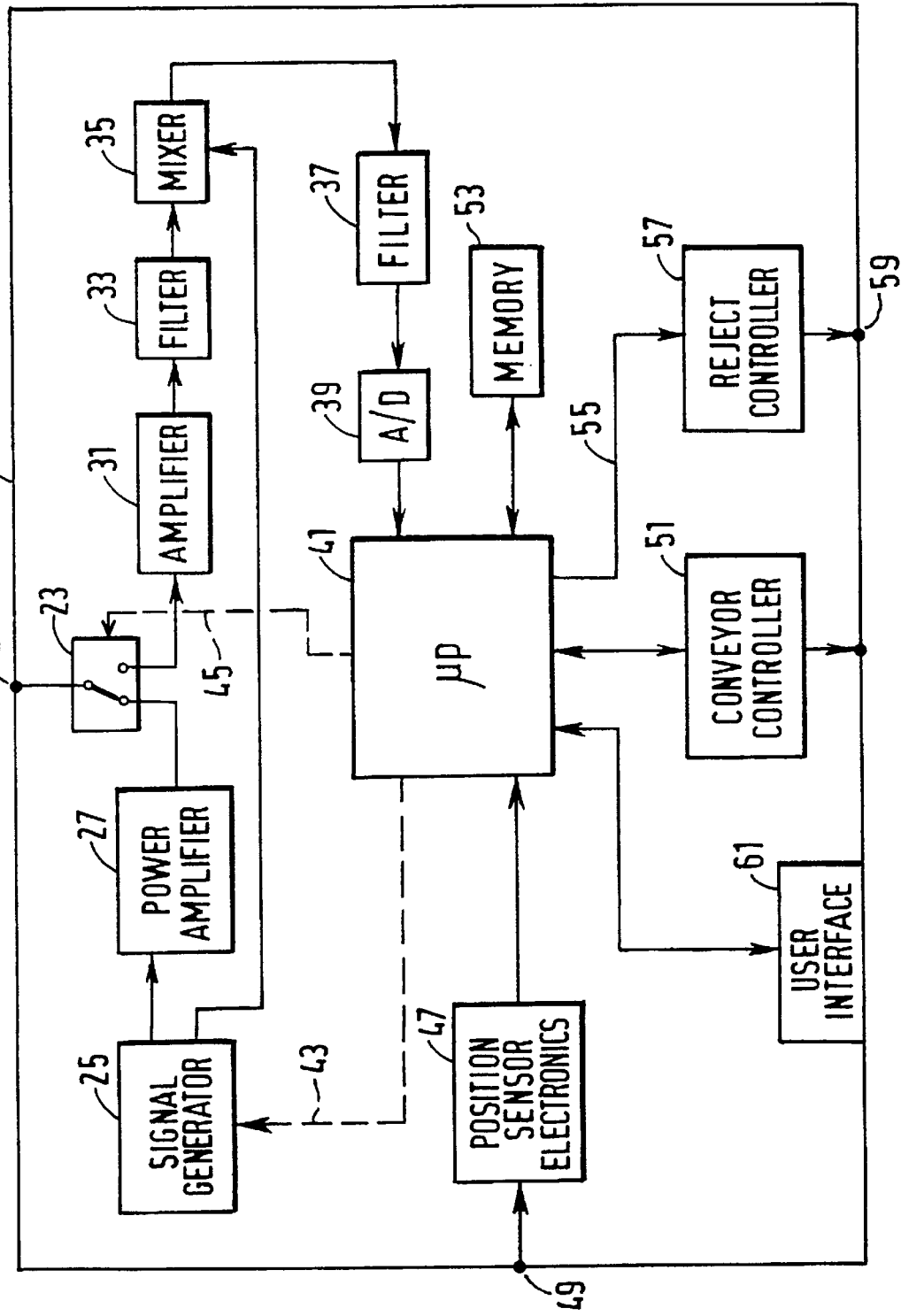
FIG. 2 is a block diagram of excitation and processing electronics which form part of and control the check weighing station shown in FIG. 1.

The operation of this embodiment will now be described in more detail with reference to FIGS. 2 to 5. FIG. 2 is a block diagram of the principal components of the computer control system 17 used in this embodiment. As shown, the control system comprises a connection terminal 21 for connecting the control system to the RF coil 15. As shown, the connection terminal 21 is connectable, through switch 23, to a signal generator 25 and a power amplifier 27 which are operable to generate and amplify respectively the excitation signal which is applied to the RF coil 15. The connection terminal 21 is also connectable, through the switch 23, to a receiving amplifier 31 which amplifies the signal received from the sample under test. This amplified signal is then filtered by the filter 33 to remove noise components and then passed to the mixer 35 where the received signal is down converted to an intermediate frequency (IF) by multiplying it with an appropriate mixing signal generated by the signal generator 25. The IF signal output by the mixer 35 is then filtered by the filter 37 to remove the unwanted components generated by the mixer 35. The filtered IF signal is then converted into a corresponding digital signal by the A/D converter 39 and then passed to the microprocessor 41.

As shown by the dashed control lines 43 and 45, the microprocessor 41 controls the operation of the signal generator 25 and the switch 23. In particular, the microprocessor 41 operates to ensure that the signal generator 25 generates the excitation signal when the filled vial 1 is at the desired location within the check weighing station 3. The microprocessor 41 knows when the vial 1 is at the correct location from a signal received from the position sensor electronics 47 which is connected, through connection terminal 49, to an optical position sensor 50 mounted in the check weighing station 3. In particular, referring to FIG. 1, when the glass vial 1 passes by the optical position sensor 50, a light beam 52 is broken. This is detected by the position sensor electronics 47 which in turn signals the microprocessor 41. Based on this information and the speed of the conveyor belt 7 (provided by the conveyor controller 51), the microprocessor determines the appropriate timing for the application of the burst of excitation current and signals the signal generator 25 accordingly.

As those skilled in the art of magnetic resonance will appreciate, it takes a finite period of time after the sample enters the homogenous static field generated by the magnet 13 for the net magnetisation of the sample to develop along the X-direction. If the excitation signal is applied to the RF coil 15 before the magnetisation has fully developed, then the strength of the signal generated by the sample will not be at its maximum. FIG. 3 illustrates the way in which the net magnetisation and thus the strength of the resultant signal produced by the sample varies with time in the static magnetic field. As shown, the plot has the general form of:

$$K_1(1\ e^{t/T_1})$$

where $K_1$ is a constant and $T_1$ is referred to as the longitudinal relaxation time and depends upon the sample being tested and the strength of the static magnetic field. Therefore, given the strength of the static magnetic field and the type of drug sample which is being tested, the relaxation time, $T_1$, can be determined. This information, combined with the speed of the conveyor belt 7, determines the minimum length of the magnet 13 in the Z-direction which is required to ensure that as large a signal as possible is generated by the sample under test.

FIG. 4 shows the 90° pulse of AC excitation current which is applied to the RF coil 15 by the signal generator 25 and the power amplifier 27. In this embodiment, the pulse of excitation current has a duration ($t_p$) of 30 microseconds and its frequency is equal to the Larmor frequency of the sample under test in the static magnetic field. In this embodiment, a capacitor (not shown) is connected across the ends of the RF coil 15 so that it is tuned to the Larmor frequency of the sample. The tuning of the RF coil 15 in this way makes the system less susceptible to electromagnetic interference or to other MR signals from nuclei with different gyromagnetic ratios. The excitation current flowing through the RF coil 15 generates a corresponding magnetic field in the Z-direction. As mentioned above, this excitation magnetic field causes the net magnetisation of the sample in the vial 1 to rotate or precess about the Z-axis at the Larmor frequency. When the excitation current is removed from the RF coil 15, the nuclei in the sample begin to relax back to their equilibrium positions, emitting RF energy at the Larmor frequency as they do so. This induces a signal in the RF coil 15 which is seen to decay exponentially and can be described as:

$$K_2 e^{-t/T_2} \quad (3)$$

where $K_2$ is a constant and $T_2$ is referred to as the transverse relaxation time and depends upon the sample being tested and not on the static field strength. FIG. 5 shows the form of the signal induced in the RF coil 15 by the sample as it relaxes back to equilibrium. As shown, the peak amplitude of the induced signal is at its maximum shortly after the excitation current stops, after which point the signal exponentially decays to zero.

As mentioned above, the peak amplitude of the signal induced in the RF coil 15 by the sample is directly proportional to the number of magnetic moments in the sample. Consequently, in this embodiment, the microprocessor 41 monitors the peak signal level which it receives from the A/D converter 39 after the excitation signal has been removed from the RF coil 15. The microprocessor 41 then compares this peak signal level with calibration data obtained by testing a similar sample or samples of known mass, to provide an indication of the mass of the sample currently being tested. In this embodiment, this calibration data is obtained from a number of similar samples of different known masses during a calibration routine before the production batch is begun and is stored in memory 53. In this embodiment, the calibration data is a function which relates the peak amplitude of the MR signal received from the sample under test to the mass of the sample.

In this embodiment, if the microprocessor 41 determines that the mass of the current sample being analysed is not of the required mass within a given tolerance, it outputs a control signal on control line 55 to the reject controller 57. The reject controller then outputs a signal to output terminal 59 which is connected to the reject station 5, for causing the reject station to remove the current vial 1 being tested from the conveyor belt 7 when it arrives at the reject station 5.

As shown in FIG. 2, the computer control system 17 also comprises a user interface 61 for allowing the user to programme into the control system 17 what the correct mass of each sample should be for a given batch of product.

A general description of a check weighing device embodying the present invention has been given above. The apparatus can be used to determine the mass of most samples provided they contain an MR responsive element in a known amount relative to the other elements in the sample. Since the hydrogen nucleus, or proton, is the element which gives the largest MR signal, due to it possessing the strongest magnetic moment, it is the one most often used. Other isotopes which have nuclear spin and will therefore provide an MR signal include: certain isotopes of nitrogen, phosphorus, sodium, potassium, fluorine and carbon and oxygen. If the check weighing station 3 described above is to be able to determine the mass of various samples using the MR signals from different MR responsive elements, then the computer control system 17 must store calibration data for each of the different samples. It must also be able to generate and receive signals at the different Larmor frequencies needed to be able to excite the different MR responsive elements.

To illustrate the operation of the present invention further, an example will now be described.

EXAMPLE

In this example, 35 milliliter capacity glass vials 1 were used each containing five milliliters of water doped with copper sulphate (to reduce the water's $T_1$ relaxation time to 100 ms). The mass of the water was determined by measuring the MR signal from the hydrogen nuclei contained in the glass vial and comparing this with the stored calibration data. The static magnet used, generated a magnetic field in the X-direction of 0.15 Tesla. The Larmor frequency of hydrogen in such a DC field is 6.38 MHz. This is calculated by multiplying the DC magnetic field strength by the gyromagnetic ratio for hydrogen (which is 42.57 MHz/Tesla). The gyromagnetic ratio for other MR responsive elements can be found in CRC Handbook of Chemistry & Physics, published by CRC Press Inc. The computer control system 17 then applied 6–7 amps of excitation AC current having a frequency of 6.4 MHz to the RF coil 15 for 30 µs. The resonance of the hydrogen atoms in the water, caused by the excitation magnetic field initially induced a few milli-volts of signal in the RF coil 15. This peak signal level was then compared with the stored calibration data (obtained by taking similar MR measurements from a number of containers having different known amounts of water) to determine the mass of water in each glass vial. The results of the technique were then compared with weighings obtained using balance scales. This comparison revealed that the MR check weighing technique provides an indication of the amount of water with an accuracy of ±2%.

In this embodiment, the microprocessor requires approximately 100 microseconds to excite and to take a reading of the peak MR signal which is received. This is then processed to determine the mass of water in the vial in real time. The theoretical limit on throughput (i.e. the number of vials which can be weighed per second) is therefore approximately 10000 vials per second, which is well within the 300 vials per minute typically required by current product lines.

As those skilled in the art will appreciate, the above technique for check weighing provides a number of significant advantages over the prior art check weighing systems. These include:

i) the technique involves a single step weighing process which can be carried out on-line—previously two weight measurements had to be obtained one before and one after filling, in order to take into account the weight of the vial;

ii) the sample can be weighed in its final packaging after it has been sealed and can therefore be weighed outside the aseptic filling area;

iii) the technique provides a contactless measure of the mass of the sample independently of the vial mass;

iv) the measurement does not affect the composition or quality of the sample and compositional information can also be obtained from the MR signal if required;

v) the technique allows for fast measurement of the sample's mass so that 100% sampling of the products can be made even at normal production throughputs;

vi) since the technique provides a measure of the sample's mass independently of the vial mass, the technique can provide an accurate determination of the mass of samples which are small relative to the vial (e.g. 200 mg sample in 10 g vials);

vii) the technique generally requires relatively low levels of static or DC magnetic field (less than 0.5 Tesla) since, in most cases, a bulk measurement over the entire sample volume is performed, thereby reducing the magnet cost and also making it possible to use permanent or electromagnets and not superconducting magnets;

viii) the technique allows a wide variety of sample sizes to be accurately weighed by the same system either using vials of the same size or using different vial sizes with different sized RF coils; and ix) the technique allows the sample to continuously move through the weighing station without stopping since the measurement can be performed in a short time relative to the throughput.

Modifications and Alternative Embodiments

In the above embodiment, a single measurement of the sample's mass was determined for each vial. The accuracy of the measurement is limited only by the random noise in the system. This can be improved by taking an average of repeated measurements. However, the rate at which measurements can be made on the same sample is determined by the $T_1$ relaxation time discussed above. In particular, after the excitation signal has been removed, it takes approximately $3T_1$ for the protons to return to their original aligned state in the static magnetic field, at which point a further burst of excitation current can be applied. This is illustrated in FIG. 6. In the example discussed above, the $T_1$ relaxation time for the water is approximately 100 milliseconds and therefore, if four measurements are taken on each sample, then the throughput can be approximately two weighings per second. Separate measurements could be obtained either by using a number of different RF coils spatially separated along the Z-direction. Alternatively, the conveyor belt could be stopped each time a vial reaches the interrogation area and multiple measurements made. Multiple measurements of the same sample may also be possible if the interrogation zone of the magnet and RF coil is large enough to allow multiple measurements to be taken considering the speed of the conveyor belt. In such an embodiment, the accuracy of the system will depend upon the homogeneity of the RF coil and the magnetic field within the interrogation zone as well as on the system signal to noise and the RF coil's fill factor. If the field patterns of the magnet and RF coil are known in advance, then this knowledge can be used to make corrections on the different measurement signals. Additionally, additional X, Y and Z coils (known in the art as shims) may also be provided to improve the homogeneity of the static magnetic field.

In the first embodiment, a single vial was located within the RF coil's interrogation zone at any one time. FIG. 7a diagrammatically illustrates the components of a check weighing station 3 which allows multiple vials to be located within the RF coil's interrogation zone at the same time and which allows a mass measurement to be made of the sample within each vial individually. To achieve this, in this embodiment, in addition to the static magnet 13 and the RF coil 15, a separate pair of coils 71 and 73 are located either side of the conveyor belt 7, which operate to provide a magnetic field gradient across the conveyor belt 7. As a result of this gradient, the static magnetic field experienced by each of the glass vials will be different and hence the Larmor frequency of the sample in each of the three vials in the interrogation zone will be different. Consequently, each vial can be interrogated separately by applying three different narrow band RF pulses at the appropriate Larmor frequency. FIG. 7b illustrates the form of a narrow band pulse which can be used to interrogate one of the three samples in the RF coil's interrogation zone and FIG. 7c shows the frequency content of the pulse. As shown, the pulse has a sinc function envelope and has a time duration ($t_p$) of approximately 4 milliseconds. It therefore has a bandwidth ($\Delta f$) of approximately 1 KHz and is centred at the appropriate Larmor frequency $f_o$. Alternatively, a broad band RF pulse could be applied over the interrogation zone and the resulting MR signals from the samples can be resolved by taking the Fourier transform of the received signal after the excitation pulse has ended, as is standard practice in MR imaging.

In the example described above with reference to FIG. 7, the gradient coils were arranged to apply a gradient in the same direction as the static magnetic field which is generated by the magnet 13. As is well known in the art of magnetic resonance imaging, gradient coils can be arranged to provide magnetic field gradients in one or more of the X, Y or Z axes so that the entire volume of the interrogation zone can be spatially resolved. FIG. 8 illustrates an embodiment where the two gradient coils 71 and 73 are provided at opposite ends of the RF coil's interrogation zone. As shown, in this embodiment, the RF coil 15 comprises three separate portions 15a, 15b and 15c. As those skilled in the art will appreciate, by applying a magnetic field gradient along the length of the conveyor belt 7 through the interrogation zone, each of the samples can be interrogated separately or simultaneously in the same way as in the embodiment described with reference to FIG. 7.

In the embodiments described with reference to FIGS. 7 and 8, a plurality of samples were located within the interrogation zone and either interrogated separately or simultaneously. In these embodiments, since each of these samples will experience a slightly different magnetic field and will be in a different position relative to the RF coil, separate calibration data can be used for each of the sensing positions in order to try to reduce errors caused by inhomogeneities in the static magnetic field or in the RF coil.

In the above embodiments, the RF coil generated a magnetic field in the Z-direction along the direction of movement of the conveyor belt 7. As those skilled in the art will appreciate, this is not essential. The RF coil can be located at any angle relative to the DC magnetic field, provided the field which it generates is relatively homogenous over the sample being tested and provided it comprises a component which is orthogonal to the static magnetic field. FIG. 9 diagrammatically illustrates an embodiment where three separate RF coils 15d, 15e and 15f are provided under the conveyor belt 7, each of which is operable to generate an AC magnetic field in the Y-direction, i.e. out of the paper. This embodiment allows the samples in three vials to be tested simultaneously. It also allows the system to interrogate the sample in each vial three times, once by each of the RF coils.

In the above embodiments, a permanent magnet was used to generate the required static magnetic field. As those skilled in the art will appreciate, electromagnets, current carrying coils or superconducting magnets could be used in place of the permanent magnet to generate the necessary DC magnetic field. Additionally, in the above embodiments, the DC magnetic field was applied across the conveyor belt in the X-direction. As those skilled in the art will appreciate, the DC magnetic field can be applied through the sample in any direction. For example, the north and south pole of the magnet may be placed above and below the conveyor with the RF coil being, for example, in the same orientation as in the first embodiment. FIG. 10 shows yet another embodiment in which a solenoid coil 75 is wound along a length of the conveyor belt 7 for generating the static magnetic field along the length of the conveyor belt 7, i.e. in the Z-direction. In this embodiment, the RF coil 15 is provided at one side of the conveyor 7 and a separate detector coil 77 is provided at the opposite side of the conveyor 7.

As those skilled in the art of MR will appreciate, there are many other configurations which will allow a measurement of the mass of the sample to be obtained.

In the above embodiments, the check weighing was performed after the vial had been filled and sealed. However, in some applications, the material which is used to seal the vial will generate an MR signal. For example, if a plastic or rubber top is used to seal the vial, then the hydrogen atoms contained in the plastic seal will also generate an MR signal which could interfere with the measurement results. There are various ways that this problem can be solved. Firstly, the check weighing station could be provided before the sealing station. However, such an embodiment is not preferred, since the check weighing station would then also have to be located within the aseptic environment of the filling station. Alternatively, this problem can be alleviated by using receive coils which are located underneath the conveyor 7, such as those shown in FIG. 9, because these coils are more sensitive to the MR signal generated by the sample than they are to the MR signal generated by the seal (because the sample is closer to the RF coil than the seal). Alternatively still, a magnetic field gradient may be applied along the length of the bottle and a narrow bandwidth RF pulse applied as in FIG. 7b, so that only the part of the bottle containing the sample is interrogated.

If the $T_2$ relaxation time for the seal is smaller than the $T_2$ relaxation time for the sample under test, then this problem can also be overcome, as illustrated in FIG. 11, by waiting a fixed period ($t_m$) before measuring the peak signal amplitude of the received MR signal. This is because the MR signal 81 from the seal will die off more quickly than the MR signal 83 from the sample. In a similar manner, if the $T_1$ relaxation time of the sample is different from the $T_1$ relaxation time of the seal, then this problem can also be overcome by firstly applying a 180° (inversion) RF pulse to the vial under test to invert the net magnetisation of the sample and the seal and then waiting until the nuclei of the seal are in such a state that when a further 90° RF interrogation pulse is applied, no signal is generated by the seal. This is illustrated in FIG. 12, which shows the signal strength 85 which can be obtained from the sample and the signal strength 87 which can be obtained from the seal after the application of the 180° pulse. As shown, because the two materials have different $T_1$ relaxation times, if a 90° interrogation pulse is applied at time $t_e$, then no signal will be generated by the seal but a signal will be generated by the sample.

In the above embodiments, a vial which does not generate an MR signal was used. As those skilled in the art will appreciate, vials which do generate an MR signal may also be used and the above techniques which were employed to separate the signals from the seal and the sample could be used to separate the signals from the sample and the vial.

In the first embodiment, a heterodyne type receiver circuit was used to receive and process the MR signal generated by the sample. As those skilled in the art will appreciate, various other types of receiver circuits, such as simple envelope detector circuits or synchronous detectors can be used. However, the heterodyne type receiver is preferred, because the microprocessor can also process the received signal to extract phase information which can be used, for example, to spatially resolve the sample in a given dimension.

In the first embodiment, the processing circuitry determined the peak signal which was received after the excitation signal has been removed from the RF coil. As those skilled in the art will appreciate, other processing techniques can be used to output a signal which varies in dependence upon the size of the sample's net magnetisation and thus the number of magnetic moments contained therein, provided the signals from the calibration samples are processed in a similar manner. For example, the microprocessor may be arranged to determine the average signal level of the received signal over a predetermined period of time.

In the above embodiment, the calibration data was stored as a function which relates the peak amplitude of the MR signal received from the sample under test to the mass or the weight of the sample. In an alternative embodiment, the calibration data may be stored as a look-up table with the peak amplitude of the MR signal received from the current sample under test being used to address the look-up table and with interpolation being used to determine the sample's mass or weight if the MR signal received from the current sample under test falls between values in the look-up table. Additionally, the calibration data may be generated using a plurality of signals of each of the different masses so that statistics can be determined which describe how the signals generated by samples of the same mass vary. These statistics can then be used to provide a possible range of error for any given measurement for a sample of unknown weight which may be used in the decision as to whether or not the sample should be rejected from the line.

As those skilled in the art will appreciate, selecting the strength of magnetic field of the DC magnet is dependent on the signal-to-noise ratio (SNR) required by the processing electronics, since the signal-to-noise ratio increases as the static magnetic field increases and a high signal-to-noise ratio will give high repeatability. Therefore, if high accuracy is required on very small samples, then a higher static magnetic field would be used than for moderate accuracy on larger samples. It is also possible to increase the signal-to-noise ratio by effectively reducing the noise level by using small RF coils in order to maximise the fill factor and thus the resultant signal level. However, there is a trade-off in this case, since good RF homogeneity over the sample volume is required to minimise the effect of repositioning inaccuracies and this is best achieved using as large an RF coil as possible.

In the above embodiment, the weight of the sample was measured using MR techniques. As those skilled in the art will appreciate, in addition to weighing each of the samples, the signal received back from the samples can be used for other quality control purposes. In this case, parameters other than the peak amplitude of the MR signal received from the sample will be used, such as the $T_2$ relaxation time.

In the above embodiments nuclear magnetic resonance techniques were used to determine the mass of a test sample. Other techniques, such as Electron Spin Resonance (ESR) also called Electron Paramagnetic Resonance and Nuclear Quadrupole Resonance (NQR) could be used. ESR is closely related to NMR but instead of the sensed signal originating in the magnetic moment of the nucleus, the signal is generated by the interaction of the magnetic moment of the electron with the external field. Because of the lighter mass of the electron as compared to the nucleus, the electron magnetic moment is much higher than the nuclear moment and therefore any ESR signal will be at a frequency several hundred times higher than the NMR signal in the same field. The above described relaxation times are also typically much shorter. Since only unpaired electrons will give rise to an ESR signal, this technique can be used on materials containing transition metals with incomplete inner electron shells, conduction electrons in metals, imperfections in insulators etc.

NQR arises when a nucleus with a quadrupole moment interacts with a non-uniform electric field of low symmetry (below cubic). NQR signals therefore only arise in solid materials and are most easily observed in crystals which are not of cubic symmetry, such as chlorine and nitrogen. The frequencies of the signals which are characteristic of the chemical compound being inspected range from a few hundred KHz to many MHz and do not require the sample to be located in a static magnetic field.

What is claimed is:

1. An apparatus for determining an on-line measure of the mass of each of a plurality of discrete samples in a production line, the apparatus comprising:

a transporter operable to transport said plurality of discrete samples along a transport path through an interrogation zone;

a static magnetic field generator operable to generate a static magnetic field in a first direction through said interrogation zone for creating a net magnetisation within a current sample located within the interrogation zone;

an alternating magnetic field generator operable to apply a pulse of alternating magnetic field in a second different direction through the interrogation zone for temporarily changing the net magnetisation of the current sample located within the interrogation zone;

a position sensor operable to sense the position of each discrete sample on said transporter as it approaches the interrogation zone and operable to output a corresponding position signal;

a controller operable to control the timing of the application of said pulse of alternating magnetic field by said alternating magnetic field generator in dependence upon the position 'signal output by said position sensor so that said pulse of alternating magnetic field is applied when said current sample is in the interrogation zone;

a sensor operable to sense energy emitted by the current sample as the net magnetisation of the current sample returns to its original state and operable to output a sensor signal in dependence thereon;

processing circuitry operable to process said sensor signal to determine a measure of the amplitude of the energy emitted by the current sample;

a memory operable to store predetermined calibration data defining a relationship between said amplitude measure and mass, which calibration data is obtained from an amplitude measure determined by said processing circuitry for one or more similar samples of known mass;

a determining device operable to determine said measure of the mass of the current sample using said calibration data and the amplitude measure output by said processing circuitry for the current sample; and wherein said static magnetic field generator is operable to generate a static magnetic field which is substantially homogeneous over a length of the transport path so that each sample is exposed to the static magnetic field for a predetermined period of time before it reaches the interrogation zone.

2. An apparatus according to claim 1, wherein said static magnetic generator comprises first and second oppositely magnetised materials which, in use, are located on opposite sides of the sample in the first direction.

3. An apparatus according to claim 1, wherein said static magnetic field generator comprises a magnet.

4. An apparatus according to claim 1, wherein said static magnetic field generator comprises at least one static loop coil and a static current generator operable to apply a static current to the static loop coil.

5. An apparatus according to claim 1, wherein said alternating magnetic field generator comprises an AC loop coil and AC current generator operable to apply an AC current to the AC loop coil.

6. An apparatus according to claim 1, wherein said second direction is substantially orthogonal to the first direction.

7. An apparatus according to claim 1, wherein energy emitted by said current sample comprises electromagnetic energy and wherein said sensor comprises a sensing loop coil which is operable to receive the emitted electromagnetic energy.

8. An apparatus according to claim 7, wherein said emitted electromagnetic energy induces a signal in said sensing loop coil that oscillates at the Larmor frequency of the sample and wherein said processing circuitry comprises a peak detector operable to detect a peak signal value of the signal induced in the sensing loop coil, as said amplitude measure.

9. An apparatus according to claim 8, wherein said peak detector is operable to determine the average peak signal value over a predetermined period.

10. An apparatus according to claim 7, wherein said alternating magnetic field generator comprises an AC loop coil and an AC current generator operable to apply an AC current to the AC loop coil, wherein said AC current generator is operable to apply a burst of AC signal to said AC loop coil and wherein said processing circuitry is operable to process the signal induced in said sensing loop coil after said burst of excitation current has ended.

11. An apparatus according to claim 8, wherein said sensing loop coil and said AC loop coil comprise the same loop coil.

12. An apparatus according to claim 1, wherein said calibration data is obtained from a plurality of similar samples of different known mass and their corresponding amplitude measures output by said processing circuitry.

13. An apparatus according to claim 12, wherein said calibration data is stored as a function relating the amplitude measure to the mass of the sample.

14. An apparatus according to claim 12, wherein said calibration data is stored as a look-up table generated from said plurality of similar samples and their corresponding amplitude measures and wherein said determining device is operable to address said look-up table with the amplitude measure output by said processing circuitry and further comprises an interpolator operable to interpolate between the entries in the look-up table to determine said measure of the mass of the current sample.

15. An apparatus according to claim 1, wherein said measure of the mass of the current sample is the weight of the current sample.

16. An apparatus according to claim 1, wherein said memory is operable to store calibration data for samples of different constitution and wherein said apparatus further comprises a selector for selecting the calibration data corresponding to the current sample under test.

17. An apparatus according to claim 16, wherein said selector comprises a user interface for allowing a user to select the calibration data for the current sample under test.

18. An apparatus according to claim 1, wherein said sample comprises a number of chemical components and wherein said alternating magnetic field generator is operable to cause the net magnetisation of one of said chemical components to change.

19. An apparatus according to claim 1, wherein each of said discrete samples is contained within a container which does not generate a magnetic resonance signal.

20. An apparatus according to claim 1, wherein each of said discrete samples is sealed within a container, wherein said seal and/or said container generate a magnetic resonance signal, and wherein said apparatus further comprises a separator operable to separate the magnetic resonance signal from the sample from the magnetic resonance signal from the seal and/or container.

21. An apparatus according to claim 1, wherein said transporter comprises a conveyor belt.

22. An apparatus according to claim 21, wherein said alternating magnetic field generator is operable to apply said field in the direction of movement of the conveyor belt.

23. An apparatus according to claim 1 wherein said static magnetic field generator is operable to generate said static magnetic field in a direction which is transverse to the transport path.

24. An apparatus according to claim 1, wherein said transporter is operable to continuously move said samples through said interrogation zone.

25. An apparatus according to claim 1, operable to determine a plurality of measurements of the mass of each sample.

26. An apparatus according to claim 1, wherein said transporter is arranged to transport a plurality of said samples through said interrogation zone at the same time.

27. An apparatus according to claim 26, further comprising a magnetic field gradient generator operable to apply a magnetic field gradient over said interrogation zone so that magnetic resonance signals from the different samples can be distinguished from a single sensor.

28. An apparatus according to claim 1, wherein said transporter is arranged to transport said samples one at a time through said interrogation zone.

29. An apparatus according to claim 1, further comprising a comparator operable to compare the measure of mass output by said apparatus with a desired sample mass and a remover operable to remove a sample from the production line if the mass of the sample is not within a given tolerance of the desired sample mass.

30. An apparatus according to claim 1, wherein said alternating magnetic field generator is operable to cause nuclei in the sample located within the interrogation zone to be excited and to thereby change the net magnetisation of the sample.

31. A method of determining an on-line measure of the mass of each of a plurality of discrete samples in a production line, the method comprising:

transporting said plurality of discrete samples along a transport path through an interrogation zone;

generating a static magnetic field in a first direction through said interrogation zone to create a net magnetisation within a current sample located within the interrogation zone;

applying a pulse of alternating magnetic field in a second different direction through the interrogation zone to temporarily change the net magnetisation of the current sample located within the interrogation zone;

sensing the position of each discrete sample along the transport path as it approaches the interrogation zone and outputting a corresponding position signal;

controlling the timing of the application of the pulse of alternating magnetic field in dependence upon the position signal output in said position sensing step, so that said pulse of alternating magnetic field is applied when said current sample is in the interrogation zone;

sensing energy emitted by the current sample as the net magnetisation of the current sample returns to its original state and outputting a sensor signal in dependence thereon;

processing said sensor signal to determine a measure of the amplitude of the energy emitted by the current sample;

storing predetermined calibration data defining a relationship between said amplitude measure and mass, which calibration data is obtained from an amplitude measure determined in said processing step for one or more similar samples of known mass;

determining the measure of the mass of the current sample using said calibration data and the amplitude measure output by said processing step for the current sample; and wherein said generating step generates a static magnetic field which is substantially homogeneous over a length of the transport path so that each sample is exposed to the static magnetic field for a predetermined period of time before it reaches the interrogation zone.

32. A method of producing sealed containers containing a predetermined amount of a sample, the method comprising the steps of:

filling the container with the predetermined amount of sample;

sealing the sample within the container;

transporting each of the filled containers along a transport path to a weighing station;

weighing the sample within each of the containers; and rejecting any containers which do not contain the predetermined amount of sample within a predetermined tolerance;

wherein said weighing step comprises:

generating a static magnetic field in a first direction through an interrogation zone to create a net magnetisation within a sample located within the interrogation zone;

applying a pulse of alternating magnetic field in a second different direction through the interrogation zone to temporarily change the net magnetisation of the current sample located within the interrogation zone;

sensing the position of each discrete sample along the transport path as it approaches the interrogation zone and outputting a corresponding position signal;

controlling the timing of the application of the pulse of alternating magnetic field in dependence upon the position signal output in said position sensing step, so that said pulse of alternating magnetic field is applied when said current sample is in the interrogation zone;

sensing energy emitted by the current sample as the net magnetisation of the current sample returns to its original state and outputting a sensor signal in dependence thereon;

processing said sensor signal to determine a measure of the amplitude of the energy emitted by the current sample;

storing predetermined calibration data defining a relationship between said amplitude measure and mass, which calibration data is obtained from an amplitude measure determined in said processing step for one or more similar samples of known mass;

determining a measure of the mass of the current sample using said calibration data and the amplitude measure output by said processing step for the current sample; and wherein said generating step generates a static magnetic field which is substantially homogeneous over a length of the transport path so that each sample is exposed to the static magnetic field for a predetermined period of time before it reaches the interrogation zone.

33. A method according to claim 32, wherein said sealing step is performed after said weighing step.

34. An apparatus for determining an indication of the mass of a sample comprising:

a signal generator operable to generate a non-uniform electric field within an interrogation zone for interacting with a sample located within the interrogation zone;

a sensor operable to sense nuclear quadrupole resonance signals generated by the interaction of the sample with the non-uniform electric field and for outputting a signal in dependence thereon;

a memory operable to store predetermined calibration data for at least one similar sample of known mass, which calibration data relates the mass of the at least one similar sample to the corresponding nuclear quadrupole resonance signal output by said sensor; and a comparator operable to compare the nuclear quadrupole resonance signal output by said sensor with said calibration data to provide said indication of the mass of the sample.

35. An apparatus according to claim 34, further comprising a transporter operable to transport said sample along a transport path through said interrogation zone.

36. An apparatus according to claim 35, wherein said transporter is operable to transport a plurality of samples through said interrogation zone and wherein said apparatus is operable to determine an indication of the mass of each of said plurality of samples.

37. An apparatus according to claim 20, wherein said seal generates a magnetic resonance signal having a $T_2$ relaxation time that is smaller than the $T_2$ relaxation time for the current sample and wherein said processing circuitry is operable to determine said amplitude measure after a predetermined period after the pulse of alternating the magnetic field has been applied to said interrogation zone.

38. An apparatus according to claim 20, wherein said seal generates a magnetic resonance signal and wherein the $T_1$ relaxation time of the sample is different from the $T_1$ relaxation time of the seal, and wherein said alternating magnetic field generator is operable to apply a first pulse of alternating magnetic field and, after a predetermined period of time is operable to generate a second pulse of alternating magnetic field at a timing so that said seal does not generate a signal in response to said second pulse.

* * * * *